US008354112B2

(12) United States Patent
Sode

(10) Patent No.: US 8,354,112 B2
(45) Date of Patent: Jan. 15, 2013

(54) GLUCOSE DEHYDROGENASE/CYTOCHROME FUSION PROTEIN

(75) Inventor: Koji Sode, Tokyo (JP)

(73) Assignees: Arkray, Inc., Kyoto (JP); Ultizyme International Ltd., Tokyo (JP)

( * ) Notice: Subject to any disclaimer, the term of this patent is extended or adjusted under 35 U.S.C. 154(b) by 894 days.

(21) Appl. No.: 10/574,085

(22) PCT Filed: Sep. 28, 2004

(86) PCT No.: PCT/JP2004/014575
§ 371 (c)(1), (2), (4) Date: Apr. 16, 2007

(87) PCT Pub. No.: WO2005/030807
PCT Pub. Date: Apr. 7, 2005

(65) Prior Publication Data
US 2007/0267301 A1   Nov. 22, 2007

(30) Foreign Application Priority Data

Sep. 30, 2003  (JP) ................. 2003-340092

(51) Int. Cl.
*A61K 39/00* (2006.01)
(52) U.S. Cl. .................................. 424/192.1
(58) Field of Classification Search .......... 424/192.1
See application file for complete search history.

(56) References Cited

U.S. PATENT DOCUMENTS

2005/0067278 A1* 3/2005 Sode .................. 204/403.04

FOREIGN PATENT DOCUMENTS

| JP | 2002-125689 A | 5/2002 |
| WO | WO-02/073181 A1 | 9/2002 |

OTHER PUBLICATIONS

Guo et al. (PNAS 101(25):9205-9210, 2004).*
Oubrie, A., et al., J. Biol. Chem., 2002, vol. 277, No. 5, pp. 3727-3732.
Okuda, J. et al., Biochem. Biophys. Res. Commun., Feb. 2004, vol. 314, No. 3, pp. 793-797.

* cited by examiner

*Primary Examiner* — Tekchand Saidha
(74) *Attorney, Agent, or Firm* — Morgan, Lewis & Bockius LLP

(57) ABSTRACT

A fusion protein of pyrroloquinoline quinone glucose dehydrogenase (PQQGDH) and a cytochrome is disclosed. PQQGDH is, for example, a water-soluble PQQGDH derived from *Acinetobacter calcoaceticus*. The cytochrome is, for example, an electron transfer domain of quinohemoprotein ethanol dehydrogenase from *Comamonas testosteroni*. The fusion protein of the present invention shows intramolecular electron transfer from PQQ, a redox center, to the cytochrome, which allow construction of a direct electron transfer-type glucose sensor which requires no electron mediators.

7 Claims, 8 Drawing Sheets

MNKHLLAKIALLSAVQLVTLSAFADVPLTPSQFAKAKSENFDKKVILSNL
NKPHALLWGPDNQIWLTERATGKILRVNPESGSVKTVFQVPEIVNDADGQ
NGLLGFAFHPDFKNNPYIYISGTFKNPKSTDKELPNQTIIRRYTYNKSTD
TLEKPVDLLAGLPSSKDHQSGRLVIGPDQKIYYTIGDQGRNQLAYLFLPN
QAQHTPTQQELNGKDYHTYMGKVLRLNLDGSIPKDNPSFNGVVSHIYTLG
HRNPQGLAFTPNGKLLQSEQGPNSDDEINLIVKGGNYGWPNVAGYKDDSG
YAYANYSAAANKSIKDLAQNGVKVAAGVPVTKESEWTGKNFVPPLKTLYT
VQDTYNYNDPTCGEMTYICWPTVAPSSAYVYKGGKKAITGWENTLLVPSL
KRGVIFRIKLDPTYSTTYDDAVPMFKSNNRYRDVIASPDGNVLYVLTDTA
GNVQKDDGSVTNTLENPGSLIKFTYKAK<u>ELgkarmpefvaqrtgqllqgv</u>
<u>kydp</u>akveagtmlyvancvfchgvpgvdrggnipnlgymdasyienlpnf
vfkgpamvrgmpdftgklsgddveslkafiqgtadairpkp

FIG. 1

```
ATGAATAAAC ATTTATTGGC TAAAATTGCT TTATTAAGCG CTGTTCAGCT AGTTACACTC
TCAGCATTTG CTGATGTTCC TCTAACTCCA TCTCAATTTG CTAAAGCGAA ATCAGAGAAC
TTTGACAAGA AAGTTATTCT ATCTAATCTA AATAAGCCGC ATGCTTTGTT ATGGGGACCA
GATAATCAAA TTTGGTTAAC TGAGCGAGCA ACAGGTAAGA TTCTAAGAGT TAATCCAGAG
TCGGGTAGTG TAAAAACAGT TTTTCAGGTA CCAGAGATTG TCAATGATGC TGATGGGCAG
AATGGTTTAT TAGGTTTTGC CTTCCATCCT GATTTTAAAA ATAATCCTTA TATCTATATT
TCAGGTACAT TTAAAAATCC GAAATCTACA GATAAAGAAT TACCGAACCA AACGATTATT
CGTCGTTATA CCTATAATAA ATCAACAGAT ACGCTCGAGA AGCCAGTCGA TTTATTAGCA
GGATTACCTT CATCAAAAGA CCATCAGTCA GGTCGTCTTG TCATTGGGCC AGATCAAAAG
ATTTATTATA CGATTGGTGA CCAAGGGCGT AACCAGCTTG CTTATTTGTT CTTGCCAAAT
CAAGCACAAC ATACGCCAAC TCAACAAGAA CTGAATGGTA AAGACTATCA CACCTATATG
GGTAAAGTAC TACGCTTAAA TCTTGATGGA AGTATTCCAA AGGATAATCC AAGTTTTAAC
GGGGTGGTTA GCCATATTTA TACACTTGGA CATCGTAATC CGCAGGGCTT AGCATTCACT
CCAAATGGTA AATTATTGCA GTCTGAACAA GGCCCAAACT CTGACGATGA AATTAACCTC
ATTGTCAAAG GTGGCAATTA TGGTTGGCCG AATGTAGCAG GTTATAAAGA TGATAGTGGC
TATGCTTATG CAAATTATTC AGCAGCAGCC AATAAGTCAA TTAAGGATTT AGCTCAAAAT
GGAGTAAAAG TAGCCGCAGG GGTCCCTGTG ACGAAAGAAT CTGAATGGAC TGGTAAAAAC
TTTGTCCCAC CATTAAAAAC TTTATATACC GTTCAAGATA CCTACAACTA TAACGATCCA
ACTTGTGGAG AGATGACCTA CATTTGCTGG CCAACAGTTG CACCGTCATC TGCCTATGTC
TATAAGGGCG GTAAAAAAGC AATTACTGGT TGGGAAAATA CATTATTGGT TCCATCTTTA
AAACGTGGTG TCATTTTCCG TATTAAGTTA GATCCAACTT ATAGCACTAC TTATGATGAC
GCTGTACCGA TGTTTAAGAG CAACAACCGT TATCGTGATG TGATTGCAAG TCCAGATGGG
AATGTCTTAT ATGTATTAAC TGATACTGCC GGAAATGTCC AAAAAGATGA TGGCTCAGTA
ACAAATACAT TAGAAAACCC AGGATCTCTC ATTAAGTTCA CCTATAAGGC TAAGGAGCTC
ggcaaggcca ggatgccgga gttcgtggcc cagcgcaccg ccagttgct gcagggcgtg
aaatcgacc ccgccaaggt cgaggccggc accatgctgt atgtggccaa ctgcgttttc
tgtcacggcg tgcctggcgt ggaccgtggc ggaaacattc ccaatctggg ttacatggac
gcgagctata tcgagaacct gccaaacttt gtcttcaagg gcccggccat ggtgcgcggc
atgccggact tcacgggcaa gttgtcgggc gatgacgtgg agtccctcaa ggccttcatc
cagggcacgg cggacgccat ccggcccaag ccctga
```

FIG. 2

```
                        SEQUENCE LISTING

<160> NUMBER OF SEQ ID NOS: 6

<210> SEQ ID NO 1
<211> LENGTH: 1776
<212> TYPE: DNA
<213> ORGANISM: Artificial Sequence
<220> FEATURE:
<223> OTHER INFORMATION: Description of Artificial Sequence: Synthetic
      DNA coding for a fusion protein

<400> SEQUENCE: 1
atgaataaac atttattggc taaaattgct ttattaagcg ctgttcagct agttacactc      60
tcagcatttg ctgatgttcc tctaactcca tctcaatttg ctaaagcgaa atcagagaac     120
tttgacaaga aagttattct atctaatcta aataagccgc atgctttgtt atggggacca     180
gataatcaaa tttggttaac tgagcgagca acaggtaaga ttctaagagt taatccagag     240
tcgggtagtg taaaaacagt ttttcaggta ccagagattg tcaatgatgc tgatgggcag     300
aatggtttat taggttttgc cttccatcct gattttaaaa ataatcctta tatctatatt     360
tcaggtacat ttaaaaatcc gaaatctaca gataaagaat taccgaacca aacgattatt     420
cgtcgttata cctataataa atcaacagat acgctcgaga agccagtcga tttattagca     480
ggattacctt catcaaaaga ccatcagtca ggtcgtcttg tcattgggcc agatcaaaag     540
atttattata cgattggtga ccaagggcgt aaccagcttg cttatttgtt cttgccaaat     600
caagcacaac atacgccaac tcaacaagaa ctgaatggta aagactatca cacctatatg     660
ggtaaagtac tacgcttaaa tcttgatgga agtattccaa aggataatcc aagtttaac      720 ggggtggtta gccatattta tacacttgga catcgtaatc cgcagggctt agcattcact     780
ccaaatggta aattattgca gtctgaacaa ggcccaaact ctgacgatga aattaacctc     840
attgtcaaag gtggcaatta tggttggccg aatgtagcag gttataaaga tgatagtggc     900
tatgcttatg caaattattc agcagcagcc aataagtcaa ttaaggattt agctcaaaat     960
ggagtaaaag tagccgcagg ggtccctgtg acgaaagaat ctgaatggac tggtaaaaac    1020
tttgtcccac cattaaaaac tttatatacc gttcaagata cctacaacta taacgatcca    1080
acttgtggag agatgaccta catttgctgg ccaacagttg caccgtcatc tgcctatgtc    1140
tataagggcg gtaaaaaagc aattactggt tgggaaaata cattattggt tccatcttta    1200
aaacgtggtg tcattttccg tattaagtta gatccaactt atagcactac ttatgatgac    1260
gctgtaccga tgtttaagag caacaaccgt tatcgtgatg tgattgcaag tccagatggg    1320
```

```
aatgtcttat atgtattaac tgatactgcc ggaaatgtcc aaaaagatga tggctcagta  1380
acaaatacat tagaaaaccc aggatctctc attaagttca cctataaggc taaggagctc  1440
ggcaaggcca ggatgccgga gttcgtggcc cagcgcaccg ccagttgct gcagggcgtg    1500 aaatacgacc ccgccaaggt cgaggccggc accatgctgt atgtggccaa ctgcgttttc   1560
tgtcacggcg tgcctggcgt ggaccgtggc ggaaacattc ccaatctggg ttacatggac  1620
gcgagctata tcgagaacct gccaaacttt gtcttcaagg gcccggccat ggtgcgcggc  1680
atgccggact tcacgggcaa gttgtcgggc gatgacgtgg agtccctcaa ggccttcatc   1740
cagggcacgg cggacgccat ccggcccaag ccctga                            1776
```

<210> SEQ ID NO 2
<211> LENGTH: 591
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 2

```
Met Asn Lys His Leu Leu Ala Lys Ile Ala Leu Leu Ser Ala Val Gln
1               5                   10                  15

Leu Val Thr Leu Ser Ala Phe Ala Asp Val Pro Leu Thr Pro Ser Gln
            20                  25                  30

Phe Ala Lys Ala Lys Ser Glu Asn Phe Asp Lys Lys Val Ile Leu Ser
        35                  40                  45

Asn Leu Asn Lys Pro His Ala Leu Leu Trp Gly Pro Asp Asn Gln Ile
    50                  55                  60

Trp Leu Thr Glu Arg Ala Thr Gly Lys Ile Leu Arg Val Asn Pro Glu
65                  70                  75                  80

Ser Gly Ser Val Lys Thr Val Phe Gln Val Pro Glu Ile Val Asn Asp
                85                  90                  95

Ala Asp Gly Gln Asn Gly Leu Leu Gly Phe Ala Phe His Pro Asp Phe
            100                 105                 110

Lys Asn Asn Pro Tyr Ile Tyr Ile Ser Gly Thr Phe Lys Asn Pro Lys
        115                 120                 125

Ser Thr Asp Lys Glu Leu Pro Asn Gln Thr Ile Ile Arg Arg Tyr Thr
    130                 135                 140

Tyr Asn Lys Ser Thr Asp Thr Leu Glu Lys Pro Val Asp Leu Leu Ala
145                 150                 155                 160

Gly Leu Pro Ser Ser Lys Asp His Gln Ser Gly Arg Leu Val Ile Gly
                165                 170                 175

Pro Asp Gln Lys Ile Tyr Tyr Thr Ile Gly Asp Gln Gly Arg Asn Gln
            180                 185                 190

Leu Ala Tyr Leu Phe Leu Pro Asn Gln Ala Gln His Thr Pro Thr Gln
        195                 200                 205

Gln Glu Leu Asn Gly Lys Asp Tyr His Thr Tyr Met Gly Lys Val Leu
    210                 215                 220

Arg Leu Asn Leu Asp Gly Ser Ile Pro Lys Asp Asn Pro Ser Phe Asn
225                 230                 235                 240

Gly Val Val Ser His Ile Tyr Thr Leu Gly His Arg Asn Pro Gln Gly
                245                 250                 255

Leu Ala Phe Thr Pro Asn Gly Lys Leu Leu Gln Ser Glu Gln Gly Pro
            260                 265                 270

Asn Ser Asp Asp Glu Ile Asn Leu Ile Val Lys Gly Gly Asn Tyr Gly
```

```
                275                 280                 285
Trp Pro Asn Val Ala Gly Tyr Lys Asp Asp Ser Gly Tyr Ala Tyr Ala
        290                 295                 300
Asn Tyr Ser Ala Ala Ala Asn Lys Ser Ile Lys Asp Leu Ala Gln Asn
305                 310                 315                 320
Gly Val Lys Val Ala Ala Gly Val Pro Val Thr Lys Glu Ser Glu Trp
                325                 330                 335
Thr Gly Lys Asn Phe Val Pro Pro Leu Lys Thr Leu Tyr Thr Val Gln
            340                 345                 350
Asp Thr Tyr Asn Tyr Asn Asp Pro Thr Cys Gly Glu Met Thr Tyr Ile
        355                 360                 365
Cys Trp Pro Thr Val Ala Pro Ser Ser Ala Tyr Val Tyr Lys Gly Gly
    370                 375                 380
Lys Lys Ala Ile Thr Gly Trp Glu Asn Thr Leu Leu Val Pro Ser Leu
385                 390                 395                 400
Lys Arg Gly Val Ile Phe Arg Ile Lys Leu Asp Pro Thr Tyr Ser Thr
                405                 410                 415
Thr Tyr Asp Asp Ala Val Pro Met Phe Lys Ser Asn Asn Arg Tyr Arg
            420                 425                 430
Asp Val Ile Ala Ser Pro Asp Gly Asn Val Leu Tyr Val Leu Thr Asp
        435                 440                 445
Thr Ala Gly Asn Val Gln Lys Asp Asp Gly Ser Val Thr Asn Thr Leu
    450                 455                 460
Glu Asn Pro Gly Ser Leu Ile Lys Phe Thr Tyr Lys Ala Lys Glu Leu
465                 470                 475                 480
Gly Lys Ala Arg Met Pro Glu Phe Val Ala Gln Arg Thr Gly Gln Leu
                485                 490                 495
Leu Gln Gly Val Lys Tyr Asp Pro Ala Lys Val Glu Ala Gly Thr Met
            500                 505                 510
Leu Tyr Val Ala Asn Cys Val Phe Cys His Gly Val Pro Gly Val Asp
        515                 520                 525
Arg Gly Gly Asn Ile Pro Asn Leu Gly Tyr Met Asp Ala Ser Tyr Ile
    530                 535                 540
Glu Asn Leu Pro Asn Phe Val Phe Lys Gly Pro Ala Met Val Arg Gly
545                 550                 555                 560
Met Pro Asp Phe Thr Gly Lys Leu Ser Gly Asp Val Glu Ser Leu
                565                 570                 575
Lys Ala Phe Ile Gln Gly Thr Asp Ala Ile Arg Pro Lys Pro
    580                 585                 590
```

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: PCR primer

<400> SEQUENCE: 3
ggccatggat aaacatttat tggctaaaat tgctttat                    38

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 4

```
gggggagctc cttagcctta taggtgaac                                              29

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 5
gggggagctc ggcaaggcca ggatgccgga                                             30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 6
ggggaagctt tcagggcttg ggccggatgg                                             30
```

GLUCOSE DEHYDROGENASE/CYTOCHROME FUSION PROTEIN

TECHNICAL FIELD

The present invention relates to a fusion protein of a glucose dehydrogenase and a cytochrome, and a glucose assay using the same.

BACKGROUND ART

Blood glucose level is an extremely crucial indicator in clinical diagnosis as an important marker for diabetes. In addition, in fermentative production using microorganisms, determination of glucose concentration is an important parameter for process monitoring. A glucose dehydrogenase having pyrroloquinoline quinone as a coenzyme (PQQGDH) has a high oxidation activity for glucose and it does not require oxygen as an electron acceptor because PQQGDH is a coenzyme-linked enzyme. Thus PQQGDH is an promising enzyme to be applied to assay techniques, for example, as a sensing element of a glucose sensor.

In order to assay glucose by an enzyme electrode having PQQGDH immobilized on its surface, it is necessary to add an electron mediator to the assay system for transferring electrons from PQQ, which is a redox center of PQQGDH, to the electrode. Accordingly, there are disadvantages in that the performance of the electrode is limited depending on the stability or solubility of the electron mediator, and the background for measurement is increased by the reaction of a contaminant with the electron mediator. Furthermore, as the electron mediator is not suitable for use in vivo, the application of PQQGDH to a glucose sensor implanted in the body has been limited. In order to solve these problems, a method of immobilizing PQQGDH on an electrode with an electron transfer protein has been proposed (WO 02/073181). In this method, however, it is necessary to use extremely excess moles of electron transfer protein, which may lead to a cost problem. Thus, there has been a demand in the art for a sensing device of a "direct electron transfer-type" glucose sensor which requires no electron mediators.

Prior art documents related to the present invention includes: J. Okuda, J. Wakai, N. Yuhashi, K. Sode, Biosensors & Bioelectronics 18 (2003) 699-704; J. Okuda, J. Wakai, K. Sode, Anal. Lett. 35 (2002) 1465-1478.

DISCLOSURE OF THE INVENTION

An object of the present invention is to provide a modified PQQGDH which allows the construction of a direct electron transfer-type glucose sensor without involving the use of electron mediators.

The present invention provides a fusion protein of pyrroloquinoline quinone glucose dehydrogenase (PQQGDH) and a cytochrome. PQQGDH is preferably a water-soluble PQQGDH derived from *Acinetobacter calcoaceticus*.

In the fusion protein of the present invention, the cytochrome has preferably been fused at the C-terminal side of PQQGDH. The cytochrome is preferably cytochrome c or cytochrome B562. Particularly preferably, the cytochrome is derived from a quinohemoprotein, which is a protein having both PQQ and a heme in one molecule. The cytochrome is preferably derived from a quinohemoprotein alcohol dehydrogenase. Particularly preferably, the cytochrome is derived from the electron transfer domain of quinohemoprotein ethanol dehydrogenase from *Comamonas testosteroni*.

Preferably the fusion protein of the present invention is either (a) or (b):

(a) a protein comprising an amino acid sequence represented by SEQ ID NO: 2;

(b) a protein comprising an amino acid sequence in which one or more amino acid residues have been deleted, substituted or added in the amino acid sequence (a) and having a glucose dehydrogenase activity and an electron transfer ability.

In another aspect, the present invention provides a gene encoding the fusion protein of the present invention, a vector and a transformant containing the gene. Preferably, the gene encoding the fusion protein has been integrated into the main chromosome of the transformant.

In still another aspect, the present invention provides an enzyme electrode comprising the fusion protein of the present invention attached to the electrode, as well as a glucose sensor utilizing such an enzyme electrode.

The present invention further provides a method of measuring the glucose concentration in a sample comprising the steps of:

contacting the sample with the enzyme electrode of the invention; and measuring electrons generated from the oxidation of glucose.

The use of the fusion protein of the present invention allows the construction of a direct electron transfer-type glucose sensor which requires no electron mediators.

BRIEF DESCRIPTION OF THE DRAWINGS

FIG. 1 shows an example of the structure of a fusion protein (SEQ ID NO: 2).

FIG. 2 shows the sequence of a gene (SEQ ID NO: 1) encoding the fusion protein shown in FIG. 1.

DETAILED DESCRIPTION OF THE INVENTION

Structure of Fusion Protein

Figure 3:
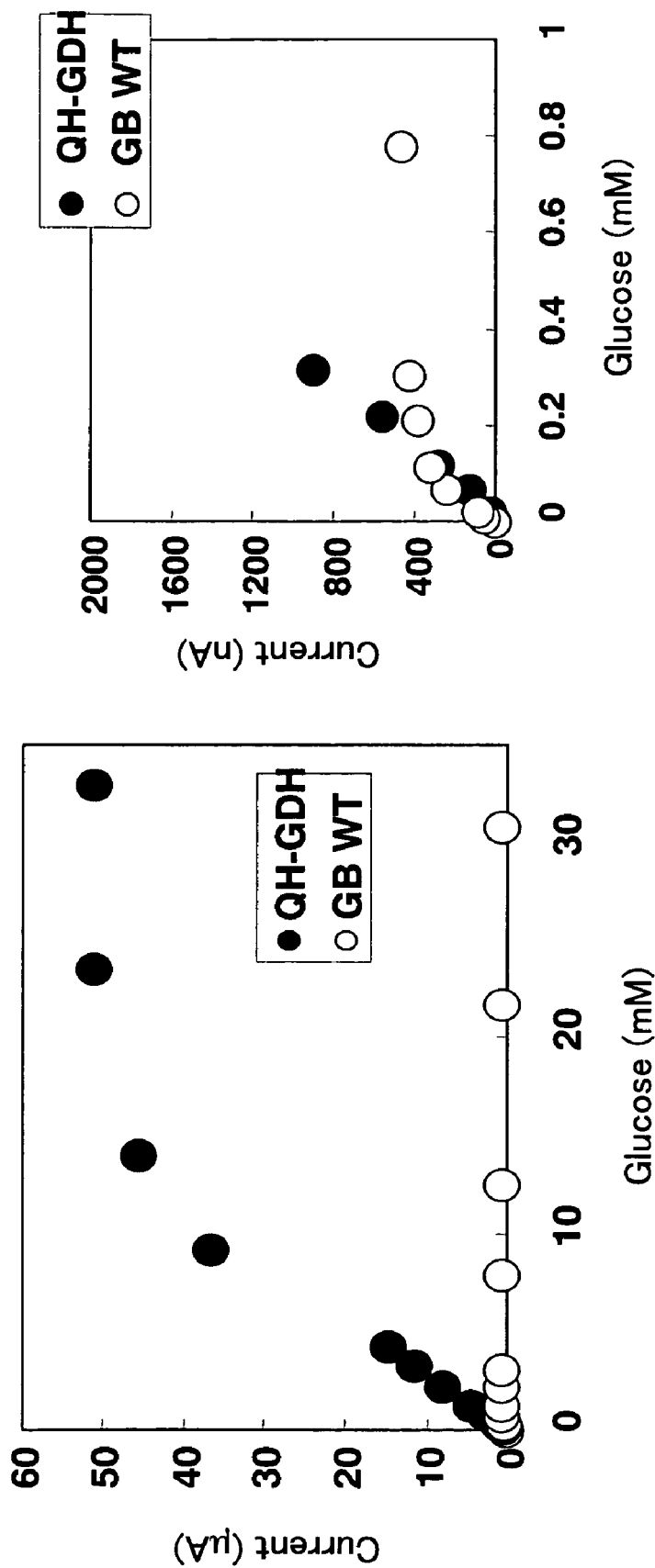
FIG. 3 shows the results of measuring the glucose concentration with the glucose sensor of the present invention in the presence of an electron acceptor.

A fusion protein of the present invention has a structure where PQQGDH and a cytochrome are bound to each other, and optionally has a linker region present between them.

PQQGDH is a glucose dehydrogenase having pyrroloquinoline quinone as a coenzyme, and catalyzes a reaction of oxidizing glucose to produce gluconolactone. Two types of PQQGDH are known: a membrane-bound enzyme and a water-soluble enzyme. The membrane-bound PQQGDH is a single-peptide protein having a molecular weight of about 87 kDa and is widely found in various gram-negative bacteria. On the other hand, the water-soluble PQQGDH has been identified in several strains of *Acinetobacter calcoaceticus*

(Biosci. Biotech. Biochem. (1995), 59 (8), 1548-1555), and the structural gene was cloned and the amino acid sequence thereof has been revealed (Mol. Gen. Genet. (1989), 217:430-436). Either of these PQQGDHs can be used in the present invention.

In the amino acid sequence of PQQGDH, part of the amino acid residues may be deleted or substituted, or another amino acid residue may be added. It has been revealed that the substitution of an amino acid residue in a specific region with another amino acid residue can improve the thermal stability of the enzyme or the affinity for a substrate while maintaining the activity of the enzyme of the oxidation of glucose (see, for example, JP-A-2000-350588, JP-A-2001-197888, JP-A-2000-312588). Such a modified PQQGDH may also be used in the fusion protein of the present invention.

The cytochrome is a heme protein having a function as an electron mediator, where one or more heme irons are covalently or non-covalently bound to a protein molecule. Many types of cytochromes including cytochrome b and cytochrome c have been isolated and identified in various organisms, and any of these cytochromes can be used in the present invention. Examples thereof include cytochrome b562 derived from bacteria such as $E.$ $coli$ strain B (Eur. J. Biochem. 202(2), 309-313 (1991)), $E.$ $coli$ strain K (Tower, M. K., Biochem. Biophys. Acta. 1143, 109-111 (1993)), $Acinetobacter$ $calcoaceticus,$ $Klebsiella$ $pneumoniae,$ $S.$ $typhi,$ $S.$ $typhinulium,$ $K.$ $pneumomiae,$ $Y.$ $pestis,$ $P.$ $multocida$ and $S.$ $pheumoniae.$ A chimeric protein produced from such a cytochrome may also be used.

Oxidoreductases having an electron transfer subunit or a heme-containing domain are known in the art. The heme protein subunit or the heme protein domain of such an enzyme is also included in the cytochrome in the present invention. In particular, the term cytochrome as used herein also includes the cytochrome domain of a quinohemoprotein, a protein having PQQ as a coenzyme, which comprises a cytochrome with PQQ and a heme iron bound to a protein molecule. Also included is a cytochrome domain of quinohemoprotein alcohol dehydrogenase, which is a quinohemoprotein having an alcohol dehydrogenase activity. Examples of such an oxidoreductase include ethanol dehydrogenase, oligosaccharide dehydrogenase and the like.

Particularly preferably, a cytochrome c domain of quinohemoprotein ethanol dehydrogenase (QHEDH) from $Comamonastes$ $testosteroni$ is used in the invention. Recently the 3D structure of QHEDH was reported (J. Biol. Chem., 277, 2002, 3727-3732). QHEDH is composed of two different domains. A first domain is a PQQ-containing catalytic domain which is composed of an eight-bladed β-propeller structure similar to PQQGDH. A second domain positioned at the C-terminal region is a cytochrome c domain. These domains are separated by a peptide linker region. In the QHEDH enzyme, an electron is transferred from PQQ, which is a redox center, to a respiratory chain via the cytochrome c, which is an electron acceptor.

In addition, the cytochrome to be used in the present invention may be a modified cytochrome in which part of the structure of a naturally occurring cytochrome has been modified. Such a modified cytochrome can be produced by substituting one or more amino acid residues of a naturally occurring cytochrome with another amino acid residue, which may or may not be a naturally occurring amino acid, or by deleting or adding one or more amino acids.

The linker region is a region that links PQQGDH to the cytochrome within the fusion protein. The linker region has a function to locate PQQGDH and the cytochrome in such a manner that the GDH activity is exerted and an electron can be efficiently transferred from PQQ to the cytochrome. The sequence of the linker region may be of a given naturally occurring or artificial amino acid sequence. For example, it may be an appropriate sequence derived from PQQGDH or the cytochrome, or may be a sequence derived from a vector used for constructing a gene encoding the fusion protein.

Method of Producing Fusion Protein

The fusion protein of the present invention can be produced by ligating in-frame a gene encoding PQQGDH and a gene encoding the cytochrome, optionally via the linker region, and allowing it to be expressed recombinantly. FIG. 1 shows one example of the fusion protein of the present invention. FIG. 2 shows the gene sequence encoding this fusion protein, where the sequence encoding PQQGDH, the linker region and the sequence encoding the cytochrome are linked to one another from the 5' side to the 3' side. The gene sequence encoding a naturally occurring water-soluble PQQGDH derived from $Acinetobacter$ $calcoaceticus$ is disclosed in Mol. Gen. Genet. (1989), 217: 430-436, and the gene sequence encoding the quinohemoprotein ethanol dehydrogenase (QHEDH) from $Comamonastes$ $testosteroni$ is disclosed in J. Biol. Chem., 277, 2002, 3727-3732. Based on these sequences, the gene encoding the fusion protein can be constructed through conventional gene manipulation techniques. Various techniques for gene manipulation are well known in the art.

The gene encoding the fusion protein obtained in this manner is inserted into an expression vector (for example, a plasmid), and the vector is transformed into an appropriate host (for example, $E.$ $coli$). A large number of vector/host systems for expressing a heterologous protein are known in the art. The host may includes various organisms such as bacteria, yeast, and cultured cells.

A transformant expressing the fusion protein is cultured and the cells are collected by centrifugation or other means from the culture medium and then disrupted by a French press or other means. The disrupted cells are centrifuged and a water-soluble fraction containing the fusion protein can be obtained. Alternatively, the expressed fusion protein can also be secreted into the culture medium by utilizing an appropriate host/vector system. The obtained water-soluble fraction is purified by ion-exchange chromatography, affinity chromatography, HPLC or other means, whereby the fusion protein of the present invention is prepared.

Enzyme Electrode

The present invention also provides an enzyme electrode having the fusion protein according to the present invention immobilized on the electrode. The enzyme electrode is an electrode in which an enzyme has been immobilized on the surface of the electrode, such as a gold electrode, a platinum electrode or a carbon electrode. The enzyme electrode is broadly used in a biosensor that utilizes the reaction specificity of an enzyme for detecting any of a variety of biologically active substances in a specific manner.

The fusion protein of the present invention attached to the enzyme electrode may recognize the presence of a test subject (for example, glucose), catalyze the redox reaction and transfer the electron generated from the reaction to the electrode.

To construct the enzyme electrode, the fusion protein of the present invention is immobilized on an electrode. Immobilization methods include, for example, a method using a crosslinking reagent, a method of entrapping the enzyme into a macromolecular matrix, a method of coating the enzyme with a dialysis membrane, a method of immobilizing the enzyme in a polymer such as a photo-crosslinking polymer, an electric conductive polymer or a redox polymer. Combinations of these methods may also be used. Typically, the fusion protein of the present invention is immobilized on a carbon electrode with glutaraldehyde, and then unreacted glutaraldehyde is blocked by a treatment with a reagent having amine groups.

Glucose Sensor

In another aspect, the present invention provides a sensor comprising the enzyme electrode of the present invention as a working electrode. The sensor as used herein means an assay system for electrochemically measuring the concentration of an objective test substance, and includes three electrodes, a working electrode (the enzyme electrode), a counter electrode (such as a platinum electrode) and a reference electrode (such as an Ag/AgCl electrode). Alternatively, it may be a two-electrode system composed of a working electrode and a counter electrode as is used in a conventional simple blood glucose monitoring system. The sensor may further comprise a constant temperature cell that holds a buffer solution and a test sample, a power source to apply voltage to the working electrode, an ampere meter, and a recorder. The sensor may be of a batch type or a flow type. In particular, the sensor is a flow-type sensor capable of continuously measuring blood glucose level, where the two-electrode system or the three-electrode system having the enzyme of the present invention immobilized thereon is inserted into a flow of continuously supplied blood sample or dialyzed sample, or into a blood sample or an interstitial fluid sample. The structure of such an enzyme sensor is well known in the art, and is described in, for example, Biosensors-Fundamental and Applications-Anthony P. F. Tuner, Isao Karube and George S. Wilson, Oxford University Press 1987.

Figure 6:
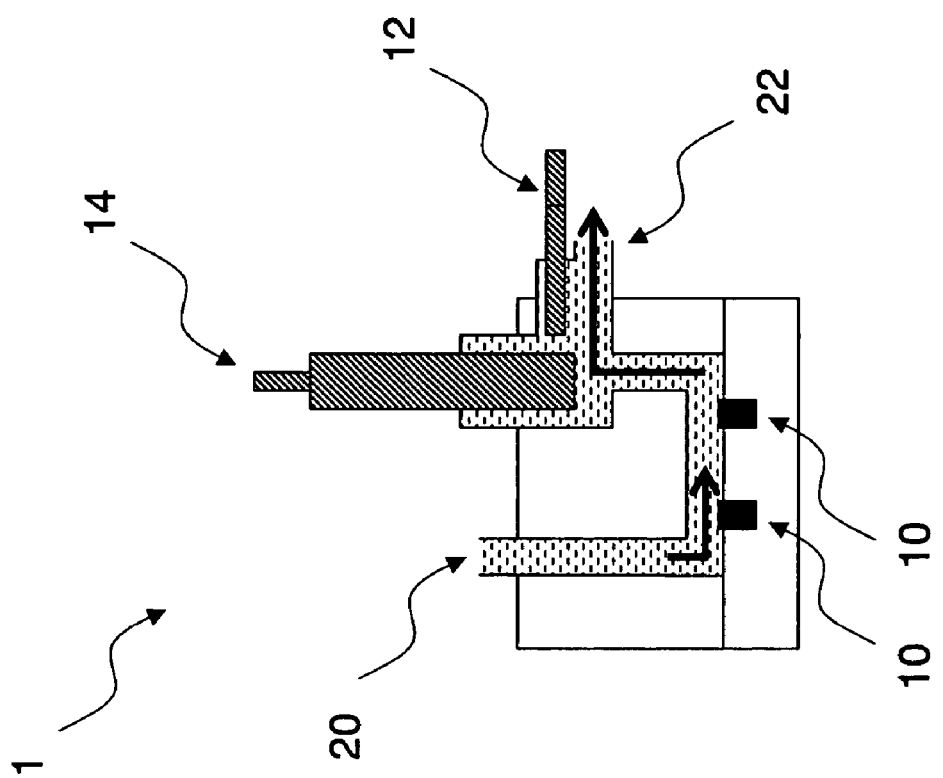
FIG. 6 shows an example of the structure of the flow cell portion of a flow-type glucose sensor.

FIG. 6 shows the schematic view of a flow cell portion of a preferred flow-type sensor of the present invention. A flow channel allowing a sample to flow at a predetermined rate is provided in a flow cell 1. A test substance diluted with an appropriate buffer solution is applied to the cell through a sample inlet port 20, and discharged from a sample outlet port 22 and directed to a sample drain. The flow cell 1 is equipped with a working electrode 10, a counter electrode 12, and a reference electrode 14, where the enzyme electrode of the present invention is used as the working electrode 10. A constant voltage is applied to the working electrode 10 from a potentiostat (not shown). While two working electrodes are shown in FIG. 6, one working electrode system may be applied.

Assay of Glucose

An assay of the glucose concentration using the glucose sensor of the present invention can be carried out as follows. A buffer solution is placed in the constant temperature cell of the sensor and a constant temperature is maintained. An enzyme electrode carrying the fusion protein of the present invention is used as the working electrode, and, for example, a platinum electrode and an Ag/AgCl electrode are used as the counter electrode and the reference electrode, respectively. A constant voltage is applied to the working electrode, and after the current reaches a steady state, a sample containing glucose is added to the constant temperature cell, and then the increase in the current is measured. The glucose concentration in the sample can be calculated according to a calibration curve generated with standard glucose solutions of known concentrations.

The entire contents of all the patents and reference documents explicitly cited in the present specification are incorporated herein by reference. In addition, the entire contents described in the specification and drawings of Japanese Patent Application No. 2003-340092, on the basis of which the present application claims a priority, are also incorporated herein by reference.

EXAMPLES

The present invention will be described in more detail with reference to the examples below, however, these examples are not to be construed to limit the scope of the invention.

Construction of Expression Vector

The structural gene of PQQGDH (without a stop codon) and the electron transfer domain of QHEDH were amplified by the PCR method from the genomes of *A. calcoaceticus* LMD 79.41 and *C. testosteroni* ATCC 15667, respectively, using primers containing a restriction enzyme recognition site at the 5'-terminus. The primers used are as follows.

```
gdhB;
sense
                                          (SEQ ID NO: 3)
5'-GGCCATGGATAAACATTTATTGGCTAAAATTGCTTTAT-3' antisense
                                          (SEQ ID NO: 4)
5'-GGGGGAGCTCCTTAGCCTTATAGGTGAAC-3' qhedhcytc domain;
sense
                                          (SEQ ID NO: 5)
5'-GGGGGAGCTCGGCAAGGCCAGGATGCCGGA-3' antisense
                                          (SEQ ID NO: 6)
5'-GGGGAAGCTTTCAGGGCTTGGGCCGGATGG-3'
```

These PCR products were inserted into the multicloning site of an expression vector, pTrc99A (Amersham Biosciences, Sweden) to prepare an expression vector pGBET. In this way, a fusion gene was constructed in which the cytochrome c domain of QHEDH was linked to the C-terminal side of PQQGDH via a linker region (FIG. 2). The sequence encoding PQQGDH is indicated by upper case letters and the sequence encoding the cytochrome is indicated by lower case letters. The restriction enzyme recognition site is shown by double underline and the linker region is shown by underline. The linker region between PQQGDH and the cytochrome c domain is composed of 24 amino acid residues derived from the native QHEDH.

The expression of ccm gene is essential for expressing the heme-containing cytochrome c in *E. coli*. Therefore, ccm is constitutively expressed by using a plasmid pEC86 (kindly gifted by Professor Linda Toeny-Meyer, ETH Switzerland) which contains the ccm gene necessary to mature the cytochrome c under the control of Km promoter.

*E. coli* DH5α was transformed with pGBET and pEC86. A transformant containing both the fusion protein expression vector and the ccm expression vector turned pink, suggesting that the mature cytochrome c is produced in the cell.

Expression and Purification of Fusion Protein

The transformant was cultured in MMI medium at 30° C. for 10 hours under semi-aerobic conditions, and the cells were collected and resuspended in a 10 mM potassium phosphate buffer solution (pH 7.0). The suspended cells were disrupted by a French press (110 MPa), ultracentrifuged (160, 500×g, 1.5 h, 4° C.), and then the supernatant was dialyzed with a 10 mM potassium phosphate buffer solution (pH 7.0). The obtained supernatant was applied to a Resource S cation-exchange column (Amersham Biosciences) which had been equilibrated with a 10 mM potassium phosphate buffer solution (pH 7.0), and the enzyme was eluted with a gradient of NaCl (5 to 150 mM) in a 10 mM potassium phosphate buffer solution (pH 7.0).

The purified enzyme showed a single band at a position of about 65 kDa on SDS-PAGE, which corresponds to the molecular weight predicted for the fusion protein. This band was also stained by heme staining.

The UV/V is spectrum of the purified fusion protein showed the peak of the oxidized type of cytochrome c at a wavelength of 411 nm. When sodium hydrosulfite (a reducing agent) was added, the fusion protein was reduced and showed peaks at 416 nm, 522 nm and 551 nm, which are typical for the reduced type of cytochrome c. From these results, it was confirmed that the fusion protein has a heme and functions as cytochrome c.

Next, in order to examine the intramolecular electron transfer between PQQ and the cytochrome c domain, glucose was added to the oxidized form of the fusion protein. When 20 mM glucose was added in the absence of an electron acceptor, the spectrum of cytochrome c changed from the oxidized form to the reduced form with time. These results indicate that the fusion protein had GDH activity, and that intramolecular electron transfer from a redox center PQQ to cytochrome c occurred in association with the oxidation of glucose.

Measurement of Enzyme Activity

The measurement of the enzyme activity was carried out in a 10 mM MOPS-NaOH buffer solution (pH 7.0) containing 0.06 mM DCIP and 0.6 mM PMS. The enzyme activity for oxidizing 1 μmol of glucose in 1 minute was defined as 1 unit. The dynamic parameters of the purified enzyme are shown in Table 1.

|  | Km (mM) | Vmax (U/mg) | V max/Km |
|---|---|---|---|
| Glucose | 23 | 3057 | 133 |
| Maltose | 15 | 1721 | 114 |
| Lactose | 19 | 1584 | 82 |

The fusion protein of the present invention has GDH activity of about 3000 U/mg of protein, which corresponds to about 70% of the activity of the wild-type PQQGDH. Furthermore, the Km value and the substrate specificity of the fusion protein for glucose were substantially the same as those reported for the wild type enzyme (Biocatal. Biotransform. 20, (2002), 405-412).

Measurement of Glucose Concentration in the Presence of Electron Acceptor

The fusion protein of the present invention (250 units; about 100 μg) or 350 U of the wild-type PQQGDH was immobilized on a glassy carbon electrode by exposing to glutaraldehyde vapor. The electrode was immersed in a 20 mM MOPS buffer solution (pH 7.0) containing 1 mM $CaCl_2$, and the response to glucose was measured at an applied voltage of +400 mV (vs. Ag/AgCl) in the presence of 10 mM potassium ferricyanide as an electron acceptor. The results are shown in FIG. 3, where "QH-GDH" indicates the fusion protein produced in this Example, and "GB WT" indicates the wild-type PPQGDH.

Under the above conditions, only a very low response was observed in the electrode on which the wild-type PQQGDH had been immobilized. In particular, the reaction with the electron acceptor was the rate-limiting step at a glucose concentration of 0.2 mM or higher, and the response was saturated. On the contrary, a very high response was obtained in the electrode on which the fusion protein of the present invention had been immobilized. In other words, glucose concentration-dependent response was observed even at a glucose concentration at which the response was saturated in the electrode having the wild-type enzyme. A good response was also exhibited at 5 to 10 mM or higher concentrations, which represent the glucose level in the human blood. These results demonstrated that the fusion protein of the present invention could give a higher response than the wild-type enzyme in the presence of an electron acceptor.

Measurement of Glucose Concentration in the Absence of Electron Acceptor

Next, the ability of the fusion protein to transfer an electron to an electrode was examined in the absence of an electron acceptor, with comparing to a mixture of the wild-type enzyme and an electron transfer protein. A 20 mM MOPS buffer solution (pH 7.0) containing 500 U of QH-GDH was mixed with carbon paste (0.5 g of graphite powder and 0.3 ml of a liquid paraffin, BAS Inc., West Lafayette, USA) and the mixture was lyophilized. The wild-type PQQGDH and an equivalent molar amount of cytb562, or an equivalent mass of BSA (bovine serum albumin) to cytb562 were used as a control. Then, the lyophilized mixture was applied to the tip of a carbon paste electrode (a diameter of 3 mm, BAS Inc.). The electrode was stored at 4° C. in a 20 mM MOPS buffer solution (pH 7.0) until use. The measurement was carried out at 25° C. in a 20 mM MOPS buffer solution (pH 7.0) containing 1 mM $CaCl_2$. An increase in the current value with the addition of glucose was detected under an applied voltage of +300 mV vs. Ag/AgCl.

Figure 4:
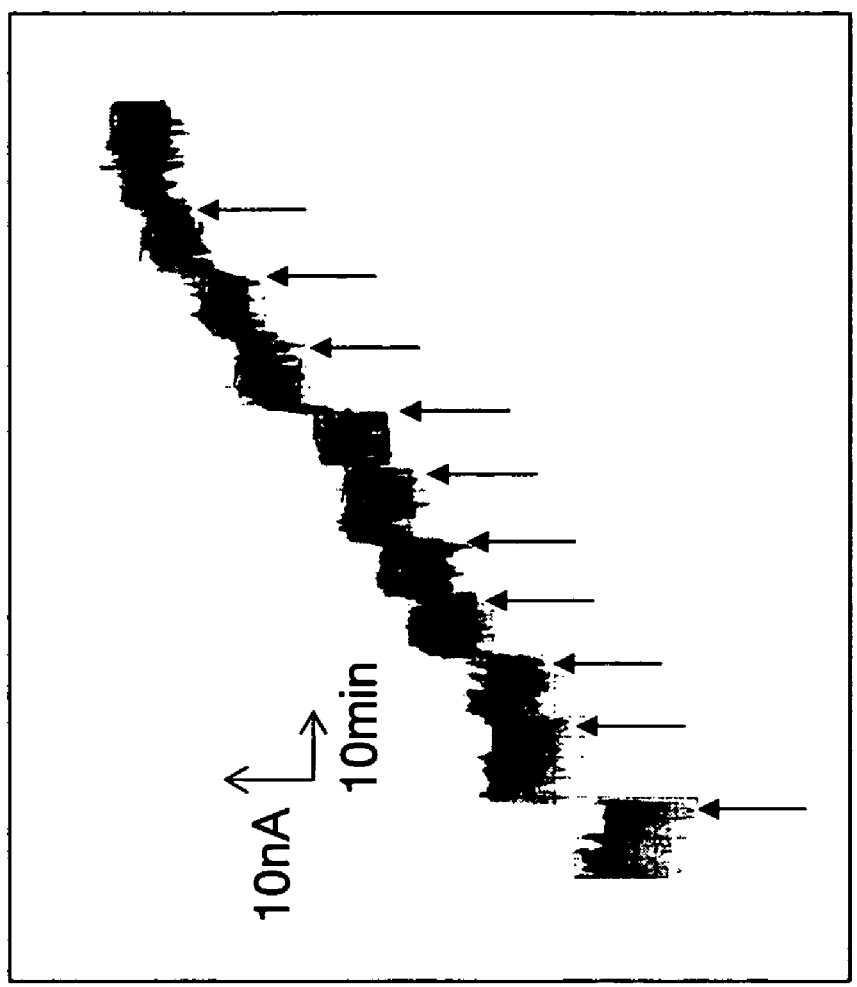
FIG. 4 shows the response current of the glucose sensor of the present invention in the absence of an electron acceptor.

The enzyme electrode on which the fusion protein of the present invention had been immobilized showed a prompt response to the addition of glucose, and the sensor signal reached a steady current within 10 seconds after the addition of glucose (FIG. 4). In FIG. 4, arrows indicate the addition of glucose. On the contrary, no increase in the current was observed in the control electrode on which the wild-type PQQGDH and cytb562 or BSA had been immobilized.

Assay of Glucose

Figure 5:
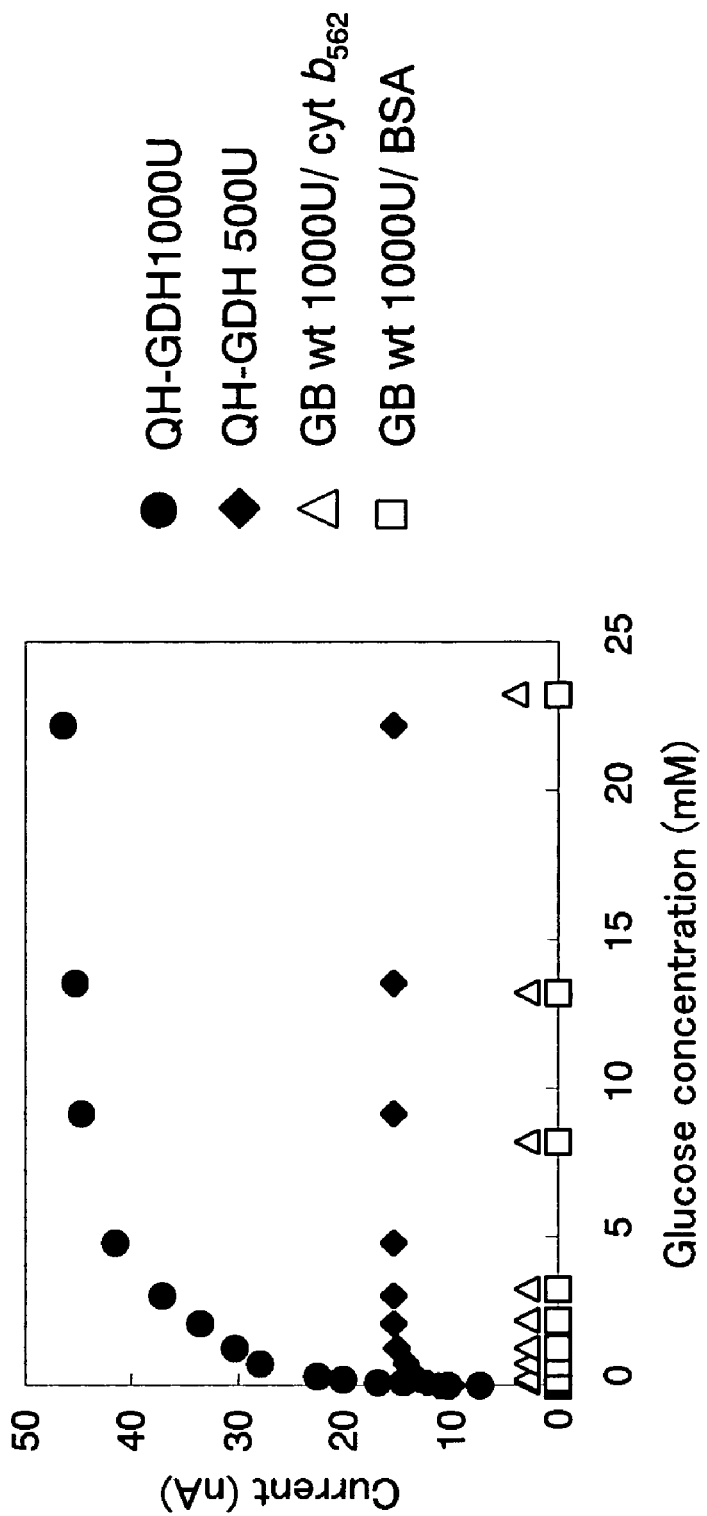
FIG. 5 shows the results of measuring the glucose concentration with the glucose sensor of the present invention in the absence of an electron acceptor.

A calibration curve for the sensor of the present invention was created using glucose solutions of various known concentrations (FIG. 5). In FIG. 5, "QH-GDH" indicates the fusion protein produced in this Example, and "GB wt" indicates the wild-type PQQGDH as a control. The observed increase in the current was proportional to the glucose concentration in the concentration range from 0.01 mM (i.e., minimum detectable concentration) to 5 mM. Furthermore, the current response was dependent on the amount of the enzyme. The sensitivity of the sensor was 9.65 $\mu M^{-1} cm^{-2}$.

Continuous Measurement of Glucose

The glucose level was continuously measured using an enzyme electrode carrying the fusion protein of the present invention. This experiment was performed for the purpose of applying the fusion enzyme of the present invention to a continuous measurement-type blood glucose measurement system that has attracted attention in recent years. The system used in this experiment was assembled in accordance with the configuration of a conventional continuous measurement-type blood glucose measurement system.

Figure 7:
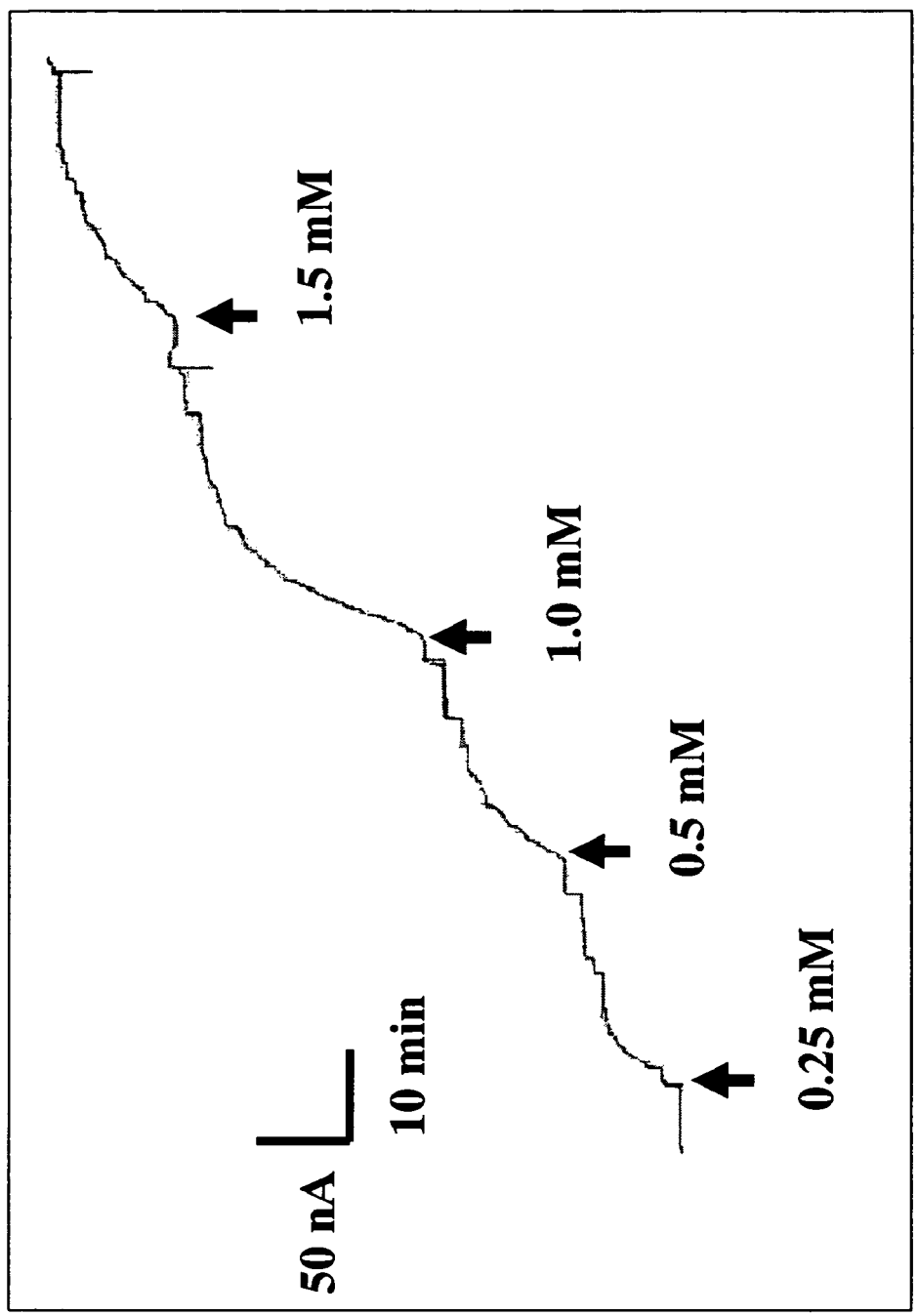
FIG. 7 shows the response current of a flow cell-type glucose sensor utilizing a fusion protein of the present invention.

The measurement was carried out using a flow cell shown in FIG. 6. A flow channel for flowing a sample is provided in a flow cell 1. A test substance diluted with an appropriate buffer solution was applied to the cell through a sample inlet port 20, and discharged through a sample outlet port 22 into a sample drain. The flow cell 1 is equipped with two working electrodes 10, a counter electrode 12, and a reference electrode 14. A constant voltage was applied to the working electrode 10 from a potentiostat (not shown). The fusion protein (750 units) was mixed with carbon paste and crosslinked to each other with glutaraldehyde and then, immobilized on the surface of the working electrode. A 100 mM potassium phosphate buffer solution (pH 7.0) containing 1 mM CaCl$_2$ was continuously supplied to the flow cell. The applied voltage was set to +300 mV vs. Ag/AgCl, and the flow rate was set to 0.5 ml/min. A sample solution with continuously variable glucose concentration was prepared by adding a solution containing 450 mg/ml glucose to the buffer solution at a given mixing ratio. The sample solution was continuously supplied to the flow cell with the enzyme electrode, and the response current was measured. The results are shown in FIG. 7. As shown in the figure, it was demonstrated that the glucose concentration could be continuously measured with the sensor based on the fusion protein of the present invention involving the direct electron transfer within the sensor, i.e., without adding an electron acceptor.

Figure 8:
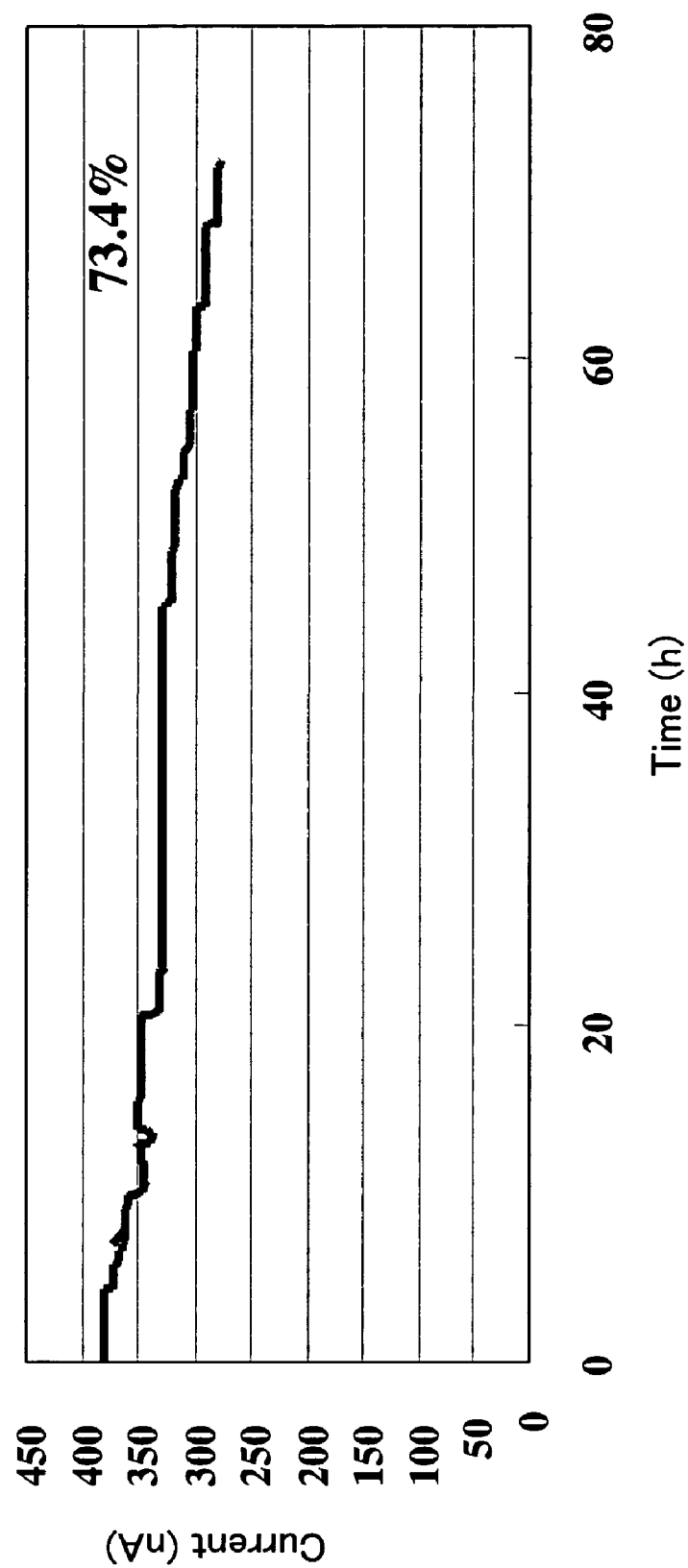
FIG. 8 shows the results of continuous running of a flow cell-type glucose sensor utilizing a fusion protein of the present invention.

Next, the long-term continuous running of the continuous glucose measurement system was investigated. When a sample containing 1 mM glucose was continuously supplied to the flow cell at a flow rate of 0.1 ml/min, a stable response was observed, and even after 72 hours, a response which was 70% or higher of the initial response value was observed (FIG. 8). These results showed that the continuous glucose measurement system utilizing the fusion protein of the present invention could be continuously operated for 3 days or longer, demonstrating that the fusion enzyme of the present invention will have a sufficient effectiveness for use in a continuous measurement-type blood glucose measurement system that has attracted attention in recent years.

INDUSTRIAL APPLICABILITY

The fusion protein of the present invention and the enzyme electrode and the biosensor using the same are useful as a direct electron transfer-type glucose sensor for measuring blood glucose level.

The invention claimed is:

1. A fusion protein of pyrroloquinoline quinone glucose dehydrogenase (PQQGDH) and a cytochrome, wherein the cytochrome has been fused to the C-terminal side of PQQGDH, and wherein the PQQGDH is either (a) or (b):
   (a) a protein comprising an amino acid sequence represented by SEQ ID NO: 2;
   (b) a protein comprising an amino acid sequence in which one amino acid residue has been deleted, substituted or added in the amino acid sequence (a) and having a glucose dehydrogenase activity and an electron transfer ability, and wherein the cytochrome is cytochrome c or cytochrome B562.

2. The fusion protein according to claim 1, wherein the cytochrome is derived from a quinohemoprotein which is a protein having both PQQ and a heme in one molecule.

3. The fusion protein according claim 1, wherein the cytochrome is derived from a quinohemoprotein alcohol dehydrogenase.

4. The fusion protein according to claim 1, wherein the cytochrome is derived from quinohemoprotein ethanol dehydrogenase from *Comamonas testosteroni*.

5. An enzyme electrode comprising the fusion protein according to claim 1 attached thereto.

6. A method of measuring the glucose concentration in a sample comprising the steps of
   contacting the sample with the enzyme electrode according to claim 5; and
   measuring electrons generated from the oxidation of glucose.

7. A glucose sensor comprising an enzyme electrode according to claim 5 as a working electrode.

* * * * *